United States Patent
Ohi et al.

(10) Patent No.: US 7,961,840 B2
(45) Date of Patent: Jun. 14, 2011

(54) DETECTOR UNIT FOR MAMMOGRAPHY, AND A NUCLEAR MEDICINE DIAGNOSTIC APPARATUS FOR MAMMOGRAPHY HAVING THE SAME

(75) Inventors: Junichi Ohi, Kyoto (JP); Masami Maekawa, Kyoto (JP); Keishi Kitamura, Kyoto (JP); Mayuka Yoshizawa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 139 days.

(21) Appl. No.: 12/521,567

(22) PCT Filed: Dec. 27, 2006

(86) PCT No.: PCT/JP2006/326131
§ 371 (c)(1),
(2), (4) Date: Jun. 27, 2009

(87) PCT Pub. No.: WO2008/081525
PCT Pub. Date: Jul. 10, 2008

(65) Prior Publication Data
US 2010/0322379 A1    Dec. 23, 2010

(51) Int. Cl.
*A61B 6/04* (2006.01)
(52) U.S. Cl. ............................................ 378/37
(58) Field of Classification Search ............ 378/37, 378/98.8; 250/370.08, 370.09
See application file for complete search history.

(56) References Cited

U.S. PATENT DOCUMENTS
2003/0194050 A1   10/2003   Eberhard et al.

FOREIGN PATENT DOCUMENTS

| CN | 1429088 A | 7/2003 |
|---|---|---|
| EP | 1 864 611 A1 | 12/2007 |
| JP | 2000-75035 A | 3/2000 |
| JP | 2003-325499 A | 11/2003 |
| JP | 2004-533607 A | 11/2004 |
| WO | WO-95/03554 A1 | 2/1995 |
| WO | WO-01/78579 A2 | 10/2001 |
| WO | WO-01/78579 A3 | 10/2001 |
| WO | WO-02/079802 A3 | 10/2002 |
| WO | WO-2006/106927 A1 | 10/2006 |

OTHER PUBLICATIONS

International Search Report for the Application No. PCT/JP2006/326131 mailed Apr. 17, 2007.
Notification of the First Office Action for Application No. 200680056788.1 from State Intellectual Property Office of the People's Republic of China dated Feb. 9, 2011.

*Primary Examiner* — Courtney Thomas
(74) *Attorney, Agent, or Firm* — Cheng Law Group, PLLC

(57) ABSTRACT

A detector unit for mammography of this invention includes a gamma-ray detector having a configuration with a cutout formed in part of a closed curve, a hollow portion thereof providing a field of view. The gamma-ray detector can easily be placed in a position where a breast and breast peripheries of a patient enter the field of view at the same time, by fitting sites of the patient not to be examined, such as a top of an arm and a shoulder, in the cutout. This allows breast tissues present in the breast and breast peripheries to be diagnosed at the same time.

36 Claims, 11 Drawing Sheets

(a)

(b)

(a)

(b)

(a)

(b)

DETECTOR UNIT FOR MAMMOGRAPHY, AND A NUCLEAR MEDICINE DIAGNOSTIC APPARATUS FOR MAMMOGRAPHY HAVING THE SAME

TECHNICAL FIELD

This invention relates to a detector unit for mammography having a gamma-ray detector for detecting gamma rays released from a patient, and a nuclear medicine diagnostic apparatus for mammography having the same.

BACKGROUND ART

Conventionally, an ordinary nuclear medicine diagnostic apparatus includes a gamma-ray detector in a circular or polygonal ring form for detecting gamma rays, and an image processor for producing an RI distribution image based on emission data obtained from the gamma-ray detector. The gamma-ray detector includes a scintillator with numerous scintillator chips for emitting light upon incidence of gamma rays, and a photomultiplier tube for converting the light emissions of the scintillator into electric signals.

A patient is placed in the hollow portion of the gamma-ray detector, and the patient is injected with a radioactive drug labeled with a positron-emitting radioisotope. The positron-emitting radioisotope distributed in the body releases two gamma rays in 180-degree opposite directions. The gamma-ray detector detects the gamma rays released from the patient. Then, the image processor collects, as emission data, events of a pair of gamma rays counted as coincidence, and produces a two-dimensional or three-dimensional RI distribution image based on this emission data. The RI distribution image produced is suitable mainly for diagnosing presence or absence, position, malignancy and so on of a tumor.

Conventionally, there is also a nuclear medicine diagnostic apparatus used mainly for radiographing the breasts (hereinafter called the nuclear medicine diagnostic apparatus for mammography). In the case of breast cancer also, it is effective to find a smaller tumor for the sake of early detection. Therefore, the size of the scintillator chips is reduced, and the gamma-ray detector is constructed to be set close to the patient (see Patent Document 1, for example).
[Patent Document 1]
Japanese Unexamined Patent Publication No. 2003-325499

DISCLOSURE OF THE INVENTION

Problem to be Solved by the Invention

However, the conventional example with such construction has the following drawback.

The conventional nuclear medicine diagnostic apparatus for mammography can place the gamma-ray detector around a breast, but the range of an armpit, a shoulder joint and so on (hereinafter called simply the breast peripheries) cannot be put into the field of view because of the gamma-ray detector hitting against the arm or shoulder. However, breast tissues exist in the breast peripheries as well as the breast, and a breast cancer can develop there. While the breast peripheries also are sites to be examined along with the breast, the conventional example has an inconvenience that the breast tissues of the breast peripheries cannot be diagnosed at the time of diagnosis of the breast.

This will be described with reference to FIG. 11. FIG. 11 is a view showing a positional relationship between the gamma-ray detector and patient M according to the conventional example. The gamma-ray detector 61 in the shape of a ring can be placed to surround a breast m1, and the breast m1 comes into its field of view. However, since breast peripheries m2 cannot be put into the field of view, as shown, the breast tissues of the breast peripheries cannot be diagnosed.

This invention has been made having regard to the state of the art noted above, and its object is to provide a detector unit for mammography and a nuclear medicine diagnostic apparatus for mammography having the same, which are capable of putting a breast and peripheries of the breast (armpit, shoulder joint and so on) into a field of view.

Means for Solving the Problem

To fulfill the above object, this invention provides the following construction.

This invention is a detector unit for mammography comprising a gamma-ray detector having a configuration with a cutout formed in part of a closed curve or a polygon having a hollow portion, the hollow portion providing a field of view.

According to the detector unit for mammography of this invention, in a case that, when placing the gamma-ray detector on a breast, the gamma-ray detector cannot closely contact the breast because sites not to be examined are obstructive, the sites not to be examined may be fitted in the cutout, thereby allowing the gamma-ray detector to contact the breast closely. Since the sites not to be examined are not obstructive, the gamma-ray detector can easily be placed in a position where the breast and breast peripheries enter the field of view at the same time. As a result, breast tissues present in the breast and breast peripheries can be diagnosed efficiently.

The invention set out in claim 2 is a detector unit for mammography comprising a gamma-ray detector having a configuration with a cutout formed in part of a ring shape having a hollow portion, the hollow portion providing a field of view.

According to the detector unit for mammography of this invention, in a case that, when placing the gamma-ray detector on a breast, the gamma-ray detector cannot closely contact the breast because sites not to be examined are obstructive, the sites not to be examined may be fitted in the cutout, thereby allowing the gamma-ray detector to contact the breast closely. Since the sites not to be examined are not obstructive, the gamma-ray detector can easily be placed in a position where the breast and breast peripheries enter the field of view at the same time. As a result, breast tissues present in the breast and breast peripheries can be diagnosed efficiently.

In this invention, it is preferred that the hollow portion is capable of receiving a breast (claim 3). The breast can be placed in the field of view conveniently.

In this invention, it is preferred that the gamma-ray detector can be positioned so that, when a top of an arm or a shoulder is inserted in the cutout, at least one of an armpit and a shoulder joint, and the breast, enter the field of view of the gamma-ray detector (claim 4). The breast and breast peripheries can be placed in the field of view of the gamma-ray detector at the same time. Thus, breast tissues present in the breast and breast peripheries can be diagnosed at the same time.

The invention set out in claim 5 is a detector unit for mammography comprising a gamma-ray detector shaped to surround a lower part of a breast, with one end region thereof placeable up to a shoulder joint above the breast, and the other end region placeable up to an armpit present laterally of the breast, wherein the gamma-ray detector has a field of view corresponding to a hollow portion formed inwardly thereof.

According to the detector unit for mammography of this invention, when placing the gamma-ray detector on a breast, the gamma-ray detector can closely contact the breast in the absence of obstructions presented by an arm and a shoulder. The breast and an armpit or/and a shoulder joint can be placed in the field of view of the gamma-ray detector. Thus, breast tissues present in the breast and breast peripheries can be diagnosed efficiently.

The invention set out in claim 6 is a detector unit for mammography comprising a gamma-ray detector shaped to extend downward from an armpit to a lower part of a breast, turn back along the lower part of the breast, and extend to a shoulder joint above the breast, wherein the gamma-ray detector has a field of view corresponding to a hollow portion formed inwardly thereof.

According to the detector unit for mammography of this invention, when placing the gamma-ray detector on a breast, the gamma-ray detector can closely contact the breast in the absence of obstructions presented by an arm and a shoulder. The breast and an armpit or/and a shoulder joint can be placed in the field of view of the gamma-ray detector. Thus, breast tissues present in the breast and breast peripheries can be diagnosed efficiently.

In this invention, it is preferred that the gamma-ray detector is placeable along a body surface of the patient (claim 7). The gamma-ray detector can be placed in closer contact with a breast and other sites.

In this invention, it is preferred that the gamma-ray detector has a horseshoe shape or a shape of letter U (claim 8).

In this invention, it is preferred that the hollow portion is substantially circular (claim 9). The substantially circular shape includes a perfect circle, a circle close to a perfect circle, and a polygon approximating to a perfect circle, and also includes a shape partly deformed with a cutout or the like.

In this invention, it is preferred that the hollow portion is 160 mm to 250 mm in diameter (claim 10). A breast and the like can be diagnosed conveniently.

In this invention, it is preferred that the cutout is 50 to 150 mm in length (claim 11). A breast and the like can be diagnosed conveniently.

In this invention, it is preferred that the hollow portion is approximately teardrop-shaped or approximately elliptical (claim 12). The breast peripheries can be put into the field of view more properly. The approximately teardrop shape or approximately elliptical shape includes a case of a part being cut off by a cutout or the like.

In this invention, it is preferred that the gamma-ray detector has a larger curvature radius in end regions thereof than in regions other than the end regions of the gamma-ray detector (claim 13). The breast peripheries can be put into the field of view more properly.

In this invention, it is preferred that the hollow portion is columnar (claim 14).

In this invention, it is preferred that the gamma-ray detector has detecting planes vertical to a bottom plane of the hollow portion (claim 15).

In this invention, it is preferred that the gamma-ray detector has detecting planes inclined relative to a bottom plane of the hollow portion (claim 16).

In this invention, it is preferred that the gamma-ray detector is displaced axially of the hollow portion (claim 17). With the gamma-ray detector twisted axially of the hollow portion, the breast peripheries can be put into the field of view properly.

In this invention, it is preferred that the gamma-ray detector is divided into two split detectors; wherein the split detectors have one ends thereof separated from each other, and the other ends joined together to render detecting planes of the split detectors continuous; the unit further comprising a split pivotal holding device for pivotably holding at least one of the split detectors, whereby the hollow portion can be enlarged and reduced in size (claim 18). The hollow portion can be enlarged or reduced in size according to the size and shape of a breast.

In this invention, it is preferred that a plate-like object is provided for closing an outside of a field of view at one side of the hollow portion (claim 19). The breast will never protrude from the field of view.

In this invention, it is preferred that an armrest member in form of a flat plate or a curved plate is provided for closing the cutout (claim 20). The armrest member provided can prevent an excessive entry of sites not to be examined such an arm and a shoulder, thereby allowing breast tissues to be diagnosed conveniently.

In this invention, it is preferred that a restricting member is disposed in the end regions of the gamma-ray detector for contacting at least one of the top of the arm and the shoulder to restrict entry of the arm and the shoulder to the hollow portion (claim 21). The restricting member provided can prevent entry of an arm and a shoulder, thereby allowing breast tissues to be diagnosed conveniently.

The invention set out in claim 22 is a detector unit for mammography comprising a gamma-ray detector having a configuration with a cutout formed in a dome shape or conical shape having a cavity, the cavity providing a field of view.

According to the detector unit for mammography of this invention, in a case that, when placing the gamma-ray detector on a breast, the gamma-ray detector cannot closely contact the breast because sites not to be examined are obstructive, the sites not to be examined may be fitted in the cutout, thereby allowing the gamma-ray detector to cover the entire breast. Since the sites not to be examined are not obstructive, the gamma-ray detector can easily be placed in a position where the breast and breast peripheries enter the field of view at the same time. As a result, breast tissues present in the entire breast and breast peripheries can be diagnosed efficiently.

In this invention, it is preferred that the cavity is capable of receiving a breast (claim 23). The breast can be placed in the field of view conveniently.

In this invention, it is preferred that, when a top of an arm or a shoulder is inserted in the cutout, at least one of an armpit and a shoulder joint, and the breast, can be positioned to enter the field of view of the gamma-ray detector (claim 24). The breast and breast peripheries can be placed in the field of view of the gamma-ray detector at the same time. Thus, breast tissues present in the breast and breast peripheries can be diagnosed at the same time.

In this invention, it is preferred that a rotary support device is provided for rotatably supporting the gamma-ray detector (claim 25). Diagnoses of the right and left breasts can be switched easily.

In this invention, it is preferred that the rotary support device supports the gamma-ray detector to be rotatable about an axis of the hollow portion (claim 26).

The invention set out in claim 27 is a nuclear medicine diagnostic apparatus for mammography comprising a detector unit for mammography according to any one of claims 1 to 26; and an image processing device for obtaining an RI distribution image based on emission data collected from the detector unit for mammography.

According to the nuclear medicine diagnostic apparatus for mammography of this invention, an RI distribution image of breast tissues present in a breast and breast peripheries can be produced. Thus, the breast tissues present in the breast and breast peripheries can be diagnosed efficiently.

Effects of the Invention

According to the detector unit for mammography of this invention, in a case that, when placing the gamma-ray detector on a breast, the gamma-ray detector cannot closely contact the breast because sites not to be examined are obstructive, the sites not to be examined may be fitted in the cutout, thereby allowing the gamma-ray detector to contact the breast closely. Since the sites not to be examined are not obstructive, the gamma-ray detector can easily be placed in a position where the breast and breast peripheries enter the field of view at the same time. As a result, breast tissues present in the breast and breast peripheries can be diagnosed efficiently.

BRIEF DESCRIPTION OF THE DRAWINGS

FIG. 2 (b) is a view in vertical section taken on line a-a of FIG. 2 (a);

FIG. 5 (b) is a view in vertical section taken on line b-b of FIG. 5 (a);

FIG. 8 (b) is a view in vertical section thereof;

DESCRIPTION OF REFERENCES

Figure 1:
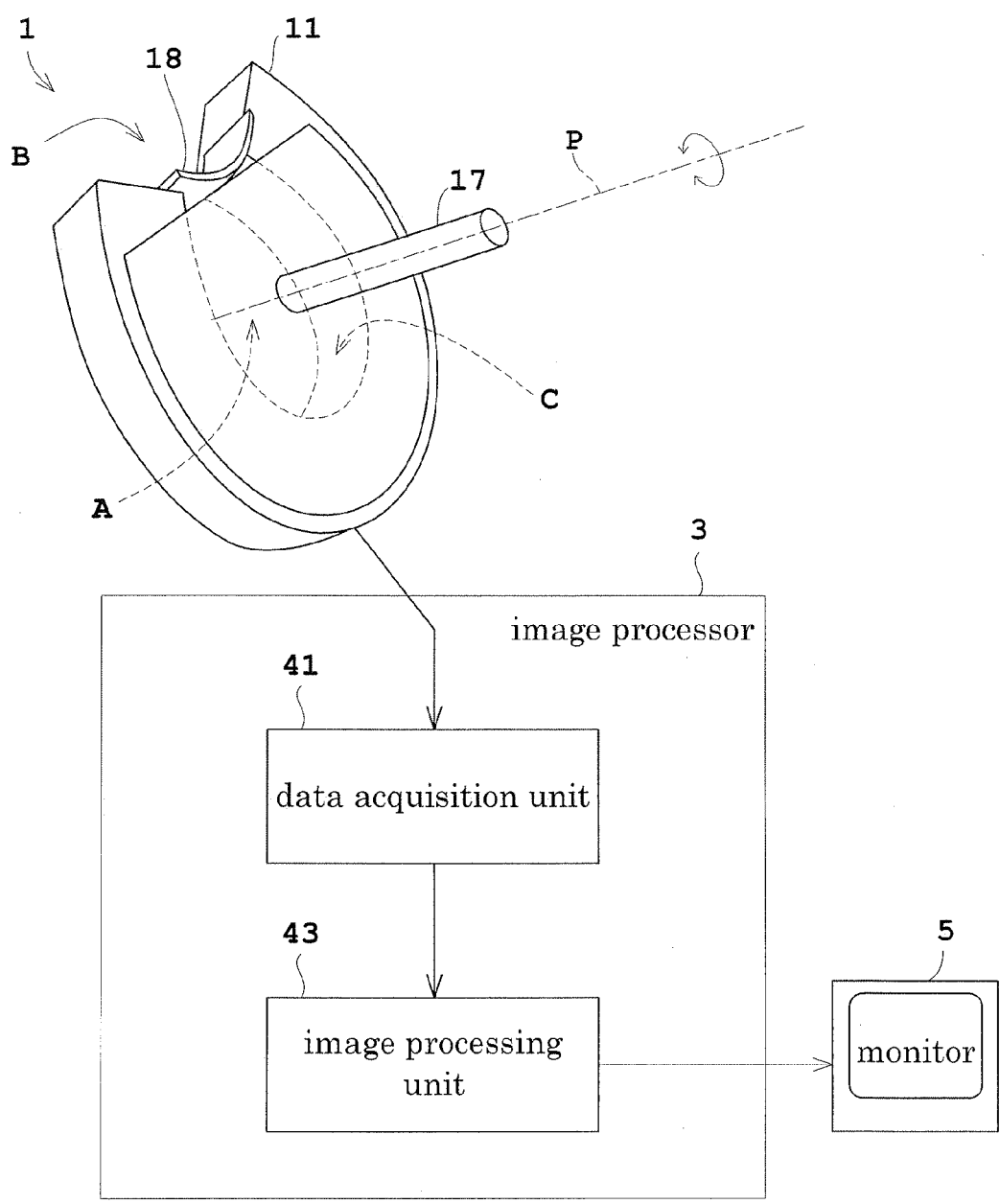
FIG. 1 is a block diagram showing an outline of a nuclear medicine diagnostic apparatus for mammography according to an embodiment.

1 . . . detector unit for mammography
3 . . . image processor
11, 12, 13, 14, 15, 16 . . . detectors (gamma-ray detectors)
17 . . . rotary support
18 . . . armrest member
19 . . . plate-like member
21 . . . detector blocks
51 . . . split pivotal holder
A hollow portion
B . . . cutout
C . . . detecting planes
P, Q . . . axis
M . . . patient

BEST MODE FOR CARRYING OUT THE INVENTION

The object of putting a breast and peripheries of the breast (armpit, shoulder joint and so on) into a field of view has been fulfilled by a detector unit for mammography comprising a gamma-ray detector having a configuration with a cutout formed in part of a closed curve or a polygon having a hollow portion, the hollow portion providing the field of view.

Embodiment

Figure 2:
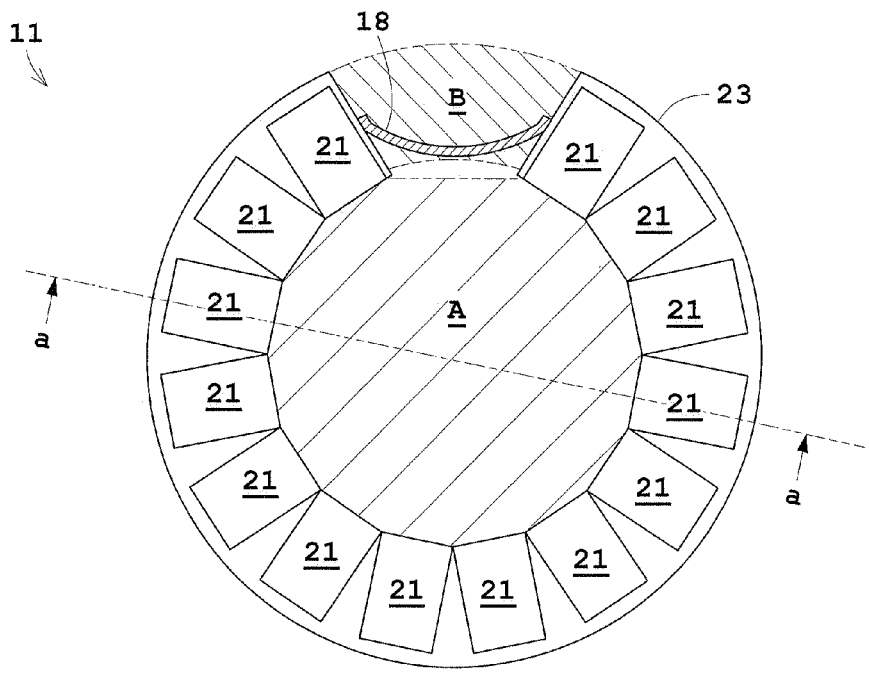
FIG. 2 (a) is a view in horizontal section of a detector.
Figure 2:
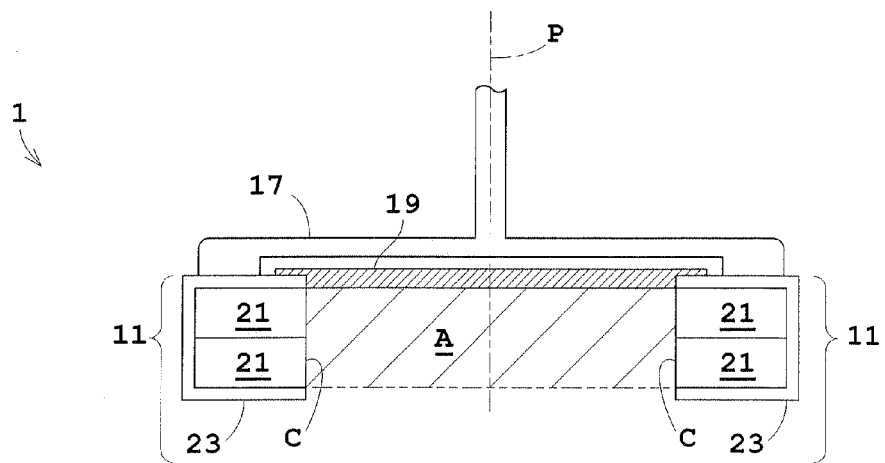
Figure 3:
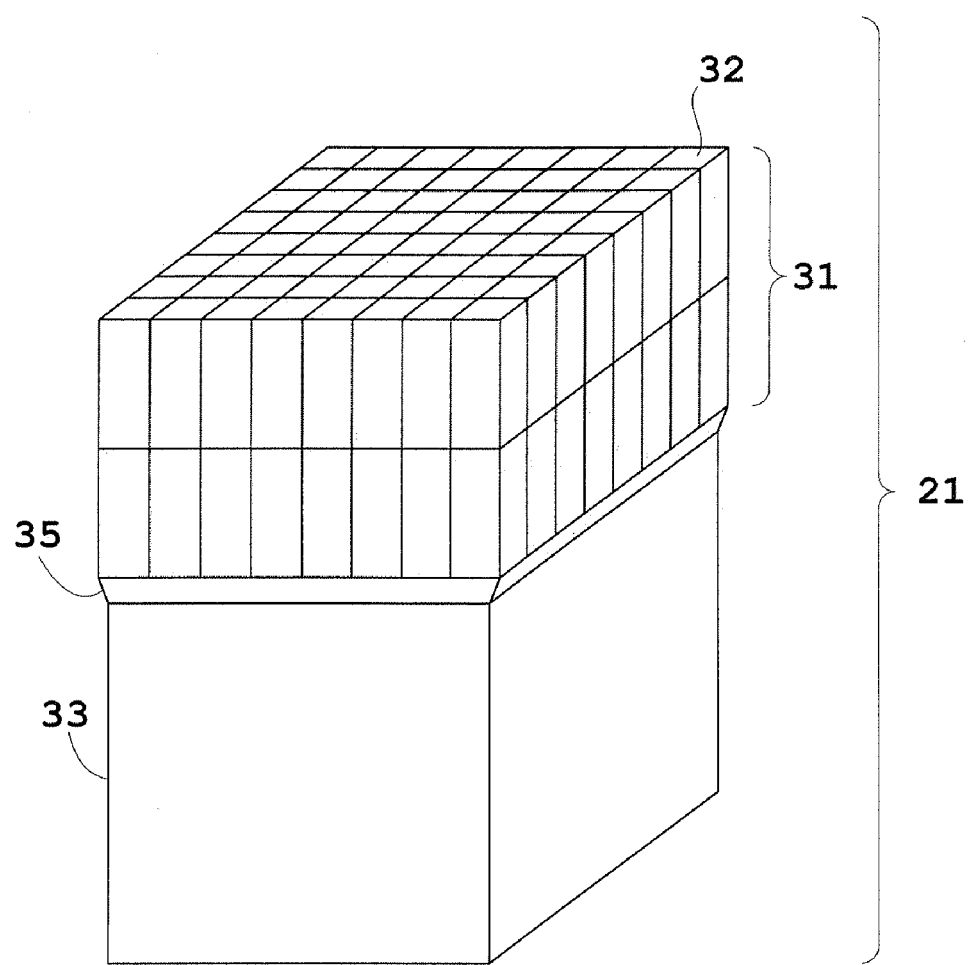
FIG. 3 is a perspective view of a detector block.

An embodiment of this invention will be described hereinafter with reference to the drawings. FIG. 1 is a block diagram showing an outline of a nuclear medicine diagnostic apparatus for mammography according to the embodiment. FIG. 2 (a) is a view in horizontal section of a detector. FIG. 2 (b) is a view in vertical section of the detector. FIG. 3 is a perspective view of a detector block.

The nuclear medicine diagnostic apparatus for mammography according to this embodiment is an apparatus for diagnosing breast tissues of a patient (human body) M, and includes a detector unit for mammography (hereinafter called simply the detector unit) 1, an image processor 3 and a monitor 5.

The detector unit 1 includes a detector 11 for detecting gamma rays, a rotary support 17 for rotatably supporting the detector 11, and an armrest member 18 for receiving an arm or the like of the patient M. The detector 11 has a configuration having a single cutout B formed in part of a closed curve having a hollow portion A in which a breast can be placed. In other words, the detector 11 is ring-shaped with a part thereof lacking. This detector 11 has detecting planes C formed inside the detector 11, with the hollow portion A providing a field of view. The detector 11 corresponds to the gamma-ray detector in this invention.

A specific configuration of the detector 11 in this embodiment will be described. The closed curve noted above is circular, and the detector 11 is formed along the curve with part of its circumference cut out. The hollow portion A has a diameter whose value is, for example, within a range of 160 mm to 250 mm. The cutout B has an arc length of 50 mm to 150 mm, for example. However, these dimensions are not limited to these ranges.

More particularly, the detector 11 includes numerous detector blocks 21 arranged along the shape of the detector 11, and a housing 23 for accommodating these detector blocks 21.

As shown in FIG. 3, each detector block 21 is constructed of a scintillator 31 for converting gamma rays into light, a photomultiplier 33 for converting the light into electric signals, and a light guide 35 for leading the light from the scintillator 31 to the photomultiplier 39. The scintillator 31 is an aggregate of scintillator chips 32 arranged in a matrix (e.g. eight rows×eight columns) which is stacked in a plurality of stages (e.g. two stages), and its upper surface acts as a detecting plane of the detector block 21.

The detecting planes C of the detector 11 noted above are formed of the detecting planes of the detector blocks 21 arranged to face the hollow portion A. Therefore, strictly speaking, the hollow portion A has a shape of a polygon approximating a circle as shown in FIG. 2. When the detector blocks 21 are stacked in two stages, the detector 11 becomes a multilayer ring with the scintillator chips 32 arranged in 16 layers. In this embodiment, as shown in FIG. 2 (b), when seen in a sectional view, the detecting planes C are planes vertical to the bottom of the hollow portion A. Therefore, the hollow portion A has a shape of an approximately cylindrical column (strictly, a polygon).

The rotary support 17 is connected to the housing 23, whereby the detector 11 is rotatable about one arbitrary axis P. In this embodiment, the one axis P coincides with the central axis of the approximately circular hollow portion A.

The armrest member 18 is a plate-like object curved to protrude to the hollow portion A. The armrest member 18 has opposite ends thereof connected to opposite end regions of the detector 11 opposed to each other across the cutout B, thereby closing the cutout B. The armrest member 18 corresponds to the armrest member in this invention, and corresponds also to the restricting member in this invention.

The detector unit 1 further includes a plate-like member 19 for closing the outside of the field of view at one side of the hollow portion A. The plate-like member 19 corresponds to the plate-like object in this invention.

The image processor 3 includes a data acquisition unit 41 and an image processing unit 43. The data acquisition unit 41 collects emission data from results of detection by the detector unit 1. The image processing unit 43 carries out a reconstruction process based on the collected emission data, to produce a two-dimensional or three-dimensional RI distribution image. The monitor 5 displays the RI distribution image produced.

The above image processor 3 is realized by a central processing unit (CPU) for reading and executing a predetermined program, and storage media such as a RAM (Random-Access Memory) and a fixed disk for storing a variety of information.

Figure 4:
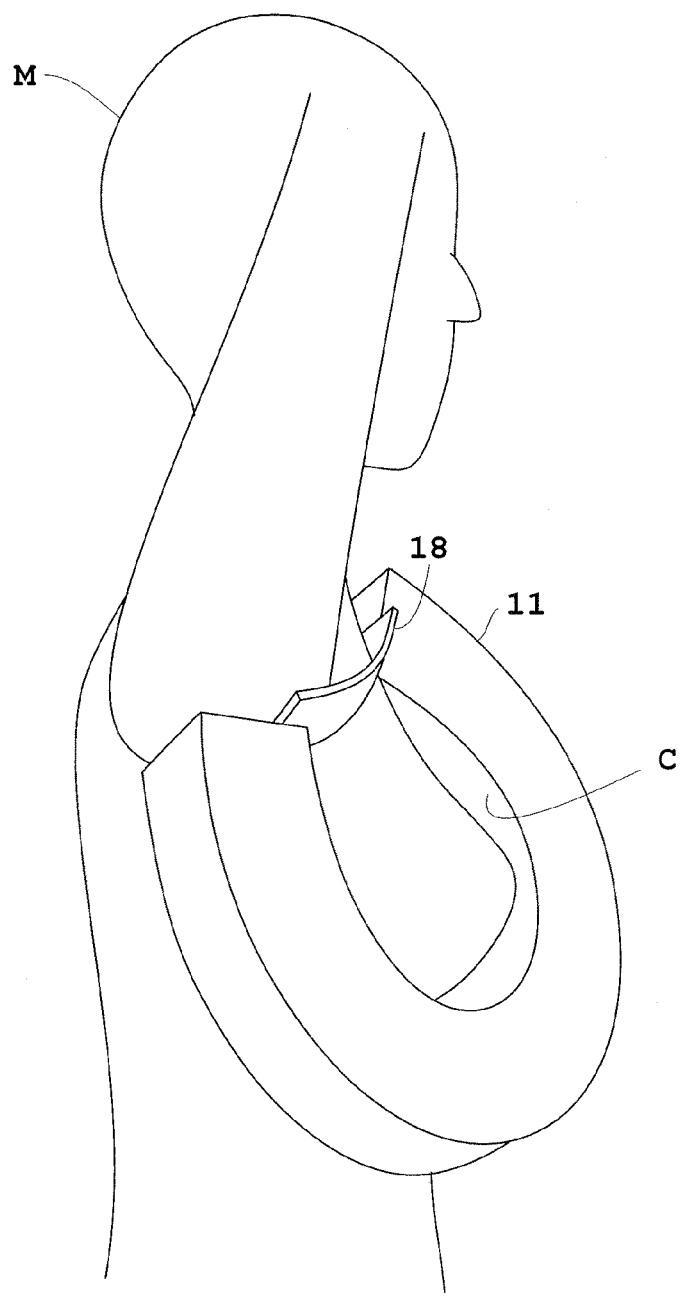
FIG. 4 is a view schematically showing a positional relationship between the detector and a patient.

Next, operation of the nuclear medicine diagnostic apparatus for mammography according to Embodiment 1 will be described. FIG. 4 is a view schematically showing a positional relationship between the detector 11 and patient M.

As shown in FIG. 4, either the right or left breast of the patient M is placed in the hollow portion A, the top of the arm or/and the shoulder on the same side as the breast of the patient M is/are inserted in the cutout B, and the arm, for example, is placed in contact with the armrest member 18. As a result, the detector 11 surrounds a lower part of the breast, with one end region of the detector 11 located in a range up to the shoulder joint above the breast, and the other end region of the detector 11 located in a range up to the armpit present laterally of the breast. Therefore, the breast peripheries such as the armpit and shoulder joint, and the breast, are placed between the detecting planes C of the detector 11 to enter the field of view of the detector 11. Because of the presence of the armrest member 18, the parts not to be examined such as the arm and shoulder do not enter the field of view of the detector 11 to an excessive extent.

Next, the patient M is injected with a radioactive drug labeled with a positron-emitting radioisotope. The positron-emitting radioisotope releases two gamma rays in 180-degree opposite directions within the patient M. The detector 11 detects gamma rays released from the breast and the peripheries of the breast and having reached the detecting planes C, and outputs electric signals.

The data acquisition unit 41 collects emission data from results of detection by the detector 11. Specifically, each electric signal outputted from the detector 11 is once recorded in the memory successively along with its position information and time information. When the detection by the detector 11 is completed, the data is read from the memory, events of coincidence are determined, and the events are counted to obtain emission data.

The image processing unit 43 carries out a reconstruction process based on the emission data collected, to produce a two-dimensional or three-dimensional RI distribution image. As an example of the reconstruction process, an iterative approximation image reconstruction (e.g. OSEM (Ordered Subset Expectation Maximization) algorithm (see Takayuki Nakamura, Hiroyuki Kudo IEEE Nuclear Science Symposium Conference Record 2005 pp. 1950-54) is preferred. According to this technique, an RI distribution image with influences of the cutout B sufficiently inhibited can be produced.

A simulation by the reconstruction technique in the OSEM algorithm has been carried out, for example, although not shown here, by uniformly arranging, as inscribed in a circle 208 mm in diameter, 12 detector blocks each having scintillator chips 1.5 mm square and 4.5 mm long stacked longitudinally in four layers and arranged 32 by 32, with one detector block omitted as the cutout B and with none omitted. It has been found, as a result, that this reconstruction technique is almost entirely free from influences of the cutout B, with spatial resolution at 70 mm from the center of the field of view being 1.3 mm for the case of providing no cutout B, and 1.6 mm for the case of providing the cutout B.

Instead of the iterative approximation image reconstruction referred to, an existing technique may be selected, such as 3D Fourier transform, 3D-FBP, rebinning, 3D reprojection or FORE (Fourier rebinning).

The RI distribution image produced is outputted to the monitor 5 as appropriate.

When the diagnosis of one of the right and left breasts is completed, the operator, for example, manually operates the rotary support 17 to rotate the detector 11 about the axis P. This changes the position of the detector 11 to facilitate diagnosis of the other breast. Then, the other breast is diagnosed through the same procedure.

Thus, according to the nuclear medicine diagnostic apparatus for mammography according to Embodiment 1, with the detector 11 which can put a breast and peripheries of the breast into the field of view at the same time, gamma rays released from the breast and breast peripheries can be detected. Therefore, presence or absence, position, malignancy and so on of a tumor can be suitably diagnosed for the breasts and also for breast tissues present around the breasts. As a result, breast cancer can be diagnosed with increased accuracy.

With the diameter of the hollow portion at 160 mm to 200 mm, and the arc length of the cutout B at 50 mm to 100 mm, a breast can be placed in the hollow portion A conveniently, and the top of the arm or the shoulder can be inserted in the cutout B.

With the detector unit 1 having the rotary support 17, the position of the detector 11 can be changed easily to facilitate diagnosis of each of the right and left breasts.

With the detector unit 1 having the plate-like member 19 for closing the outside of the field of view at one side of the hollow portion, a breast is prevented from protruding from the field of view, and the entire breast can be diagnosed conveniently.

The detector unit 1 with the armrest member 18 can prevent an excessive entry of an arm, for example. Since the patient M can take a comfortable position, the burden of the patient M can be reduced.

With the image processor 3, RI distribution images can be produced appropriately.

This invention is not limited to the foregoing embodiment, but may be modified as follows:

(1) In the foregoing embodiment, the closed curve is a circle on the same plane, and the detector 11 is formed along the curve with part of its circumference cut out. This is not limitative. As long as it is a closed curve or a polygon having a cutout in part thereof, various shapes can be selected as appropriate. Therefore, it is not limited to being on the same plane, either.

Figure 5:
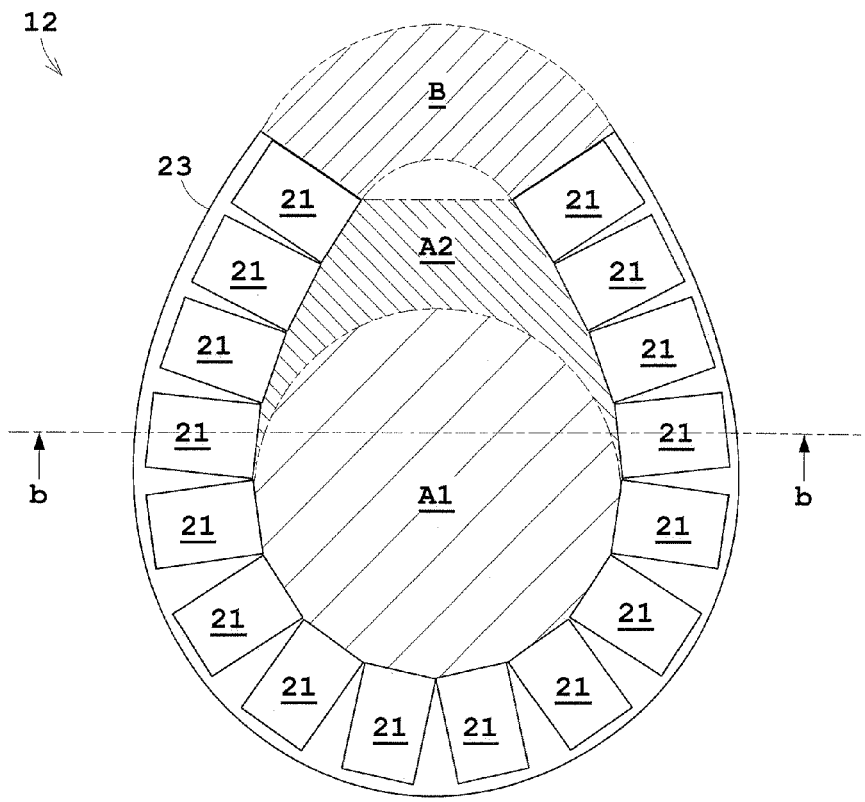
FIG. 5 (a) is a view in horizontal section of a detector according to a modified embodiment.
Figure 5:
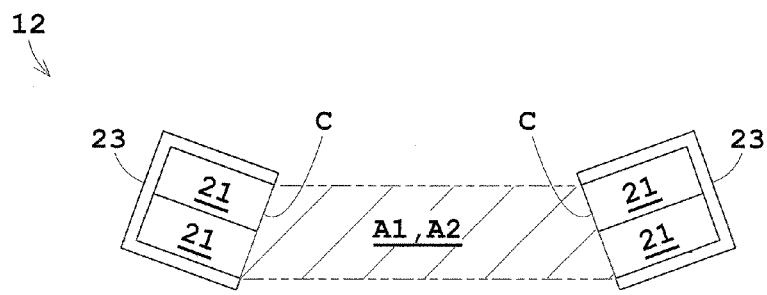
Figure 6:
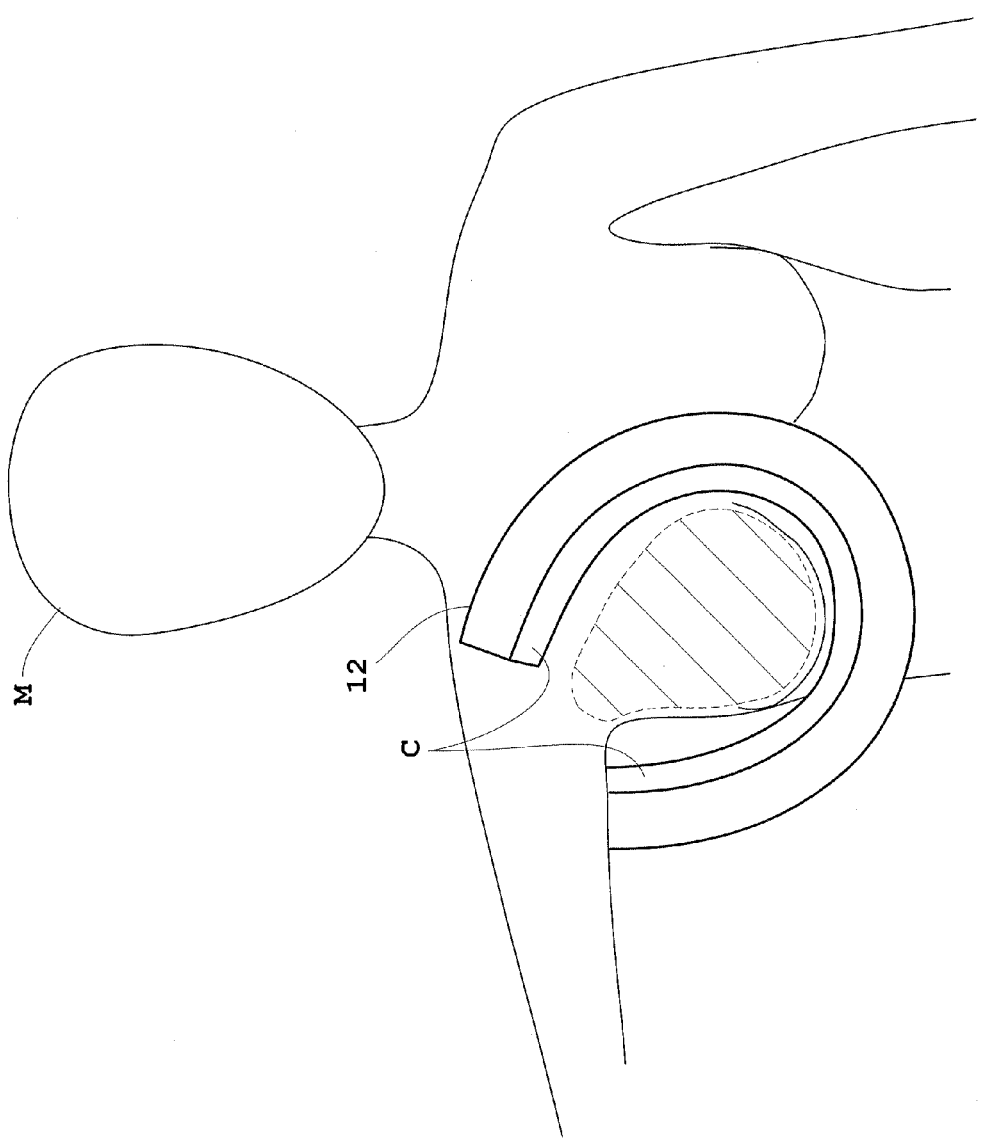
FIG. 6 is a view schematically showing a positional relationship between the detector and a patient according to the modified embodiment.

Reference is made to FIGS. 5 and 6. FIG. 5 (*a*) is a view in horizontal section of a detector according to a modified embodiment. FIG. 5 (*b*) is a view in vertical section thereof. FIG. 6 is a view schematically showing a positional relationship between a detector 12 and a patient M according to this modified embodiment. As shown in FIGS. 5 and 6, the closed curve is teardrop-shaped, and the detector 12 has a shape extending along the curve with part of the tear-drop-shaped outline cut out. A cutout B is formed adjacent an upper end where the teardrop-shaped outline tapers. The field of view of the detector 12 corresponds to areas of hollow portions A1 and A2. Incidentally, where the detector 11 described in Embodiment 1 is comparable with the width of the detector 12, the field of view of the detector 11 can be only a field of view approximately corresponding to the hollow portion A1. Thus, with the detector 12 according to the modified embodiment, the hollow portion A2 in addition to the hollow portion A1 can provide the field of view. A larger range of breast peripheries can be put into the field of view (in FIG. 6, a breast and breast peripheries included in the field of view of the detector 12 are specified by hatching).

Besides the shape of the detector 12 shown in the modified embodiment shown in FIGS. 5 and 6, a detector may be provided to have a horseshoe shape, a shape of letter U or a shape of letter C. Instead of the teardrop shape described referring to FIG. 5, a detector may be selected to have an elliptical shape, rugby ball shape or various other outline shapes with a cutout.

Figure 7:
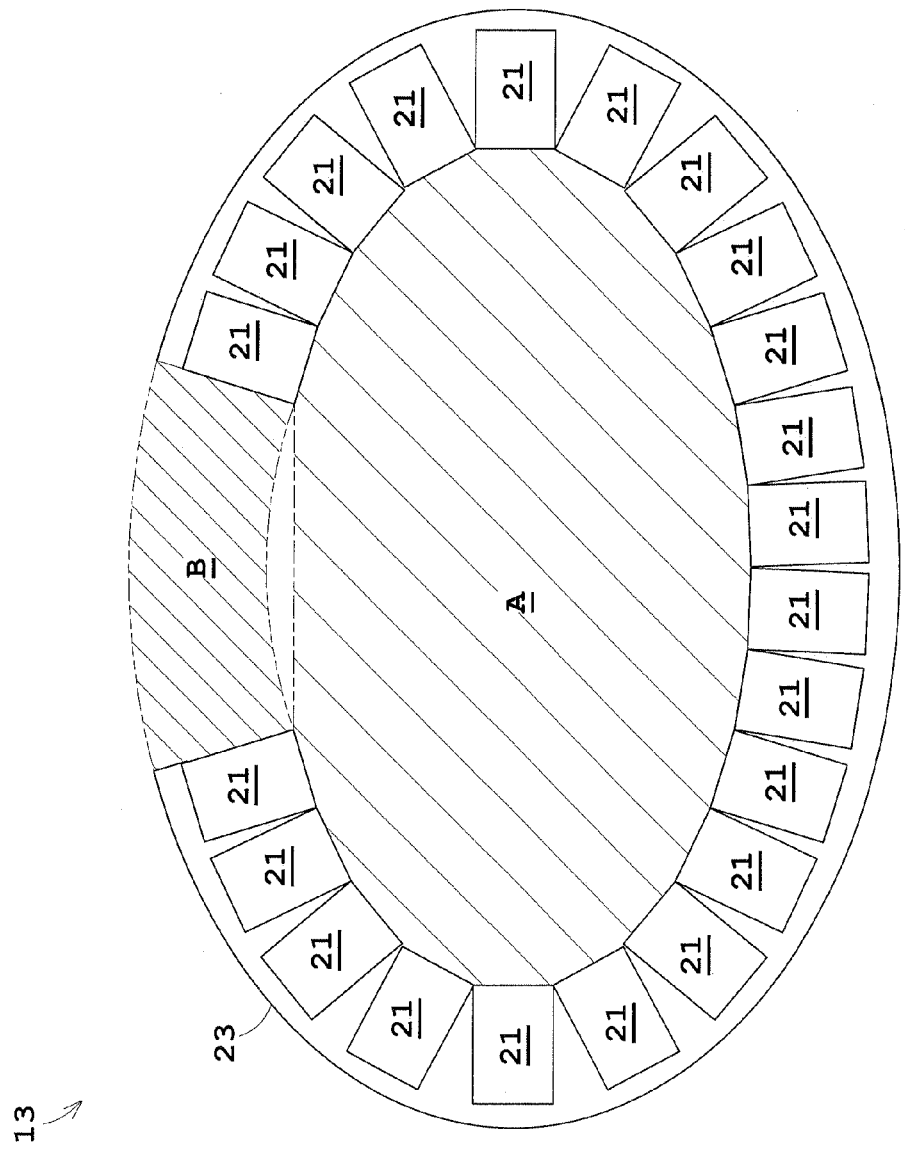
FIG. 7 is a view in horizontal section of a detector according to a modified embodiment.

(2) Although, in the foregoing embodiment, the position of the cutout B has not particularly been described, but this is a matter selectable as appropriate. For example, a position in the longer direction, shorter direction or other position of the outline of the closed curve, may be selected as appropriate. FIG. 7 refers. FIG. 7 is a view in horizontal section of a detector according to a modified embodiment. A detector 13 shown has a shape of an elliptical outline with part thereof cut out. Here, a cutout B is formed in a portion where the minor axis of the ellipse intersects the elliptical outline.

(3) The shape of the detector 11 may be varied such that the curvature radius in the opposite end regions of the detector 11 opposed to each other across the cutout B is larger than in regions other than the opposite end regions of the detector 11. Or, where the opposite end regions of the detector 11 are not curved, a modification may be made such that the detecting planes C in the opposite end regions opposed to each other across the cutout B are parallel to each other or in a near parallel relationship. Then, the breast peripheries can be put properly and extensively into the field of view. Specifically, the modified embodiment described in FIGS. 5 and 6 can be given as an example. That is, the detector 12 shown in FIG. 5 has a curvature radius in the opposite end regions of the detector 12 opposed to each other across the cutout B which is larger than in regions other than the opposite end regions of the detector 12.

(4) In the embodiment described hereinbefore, the hollow portion A is columnar, but this is not limitative. For example, a modification may be made to incline the detecting planes C of the detector 11 relative to the bottom of the hollow portion A. Specifically, as in the detector 12 shown in FIG. 5 (*b*), the detecting planes may be inclined relative to the bottom of the hollow portions A1 and A2. This allows the detecting planes to be placed close to the breast and breast peripheries.

(5) In the embodiment described hereinbefore, the detector 11 has a shape of a closed curve with a part thereof cut out, but this is not limitative. For example, the detector may have a shape forming a cutout in the shape of a dome having a cavity which can receive a breast therein. The dome shape may be semispherical, for example. The dome shape may be changed to a conical shape such as of a circular cone or pyramid.

Figure 8:
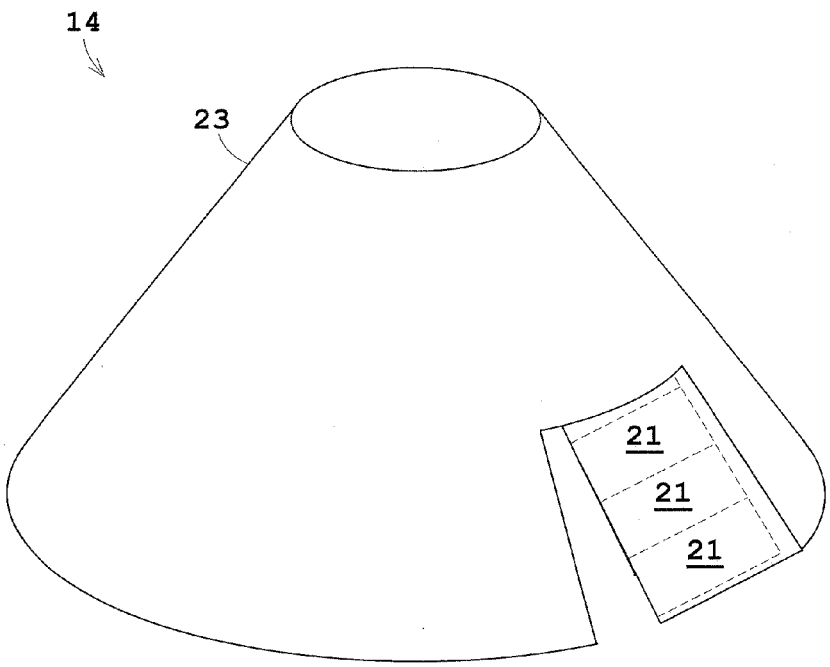
FIG. 8 (a) is a plan view of a detector according to a modified embodiment.
Figure 8:
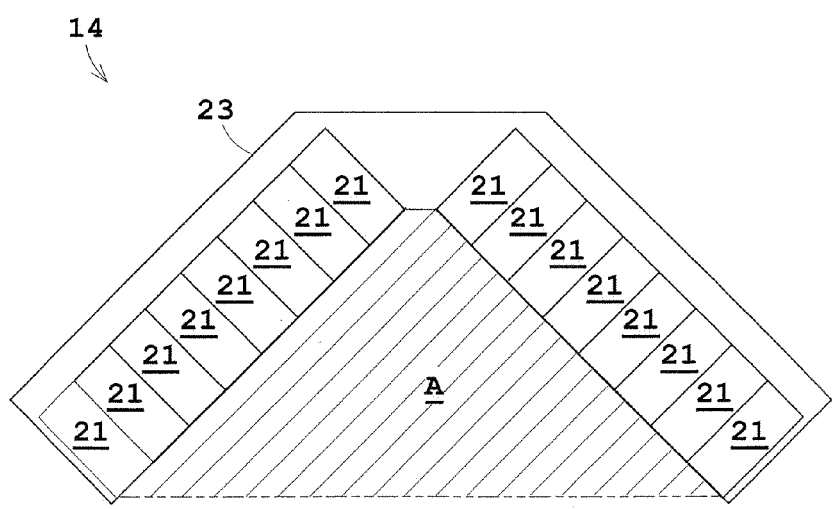

FIG. 8 (*a*) is a plan view of a detector according to a modified embodiment. FIG. 8 (*b*) is a view in vertical section thereof. In this modified embodiment, a detector 14 is constructed with a hollow portion A in a shape of a cone (approximately circular cone-shaped). Specifically, detecting planes C of the detector 14 are inclined relative to the bottom of the hollow portion A, with an upper part of the hollow portion A closed. With the detector 14 constructed in this way, an entire breast can be accommodated in the hollow portion A, and therefore the entire breast can easily be put into the field of view. The plate-like member 19 described in Embodiment 1 is dispensable.

(6) In the embodiment described hereinbefore, the hollow portion A formed in the detector 11 is fixed. A detector may be constructed to have a hollow portion A variable in size.

Figure 9:
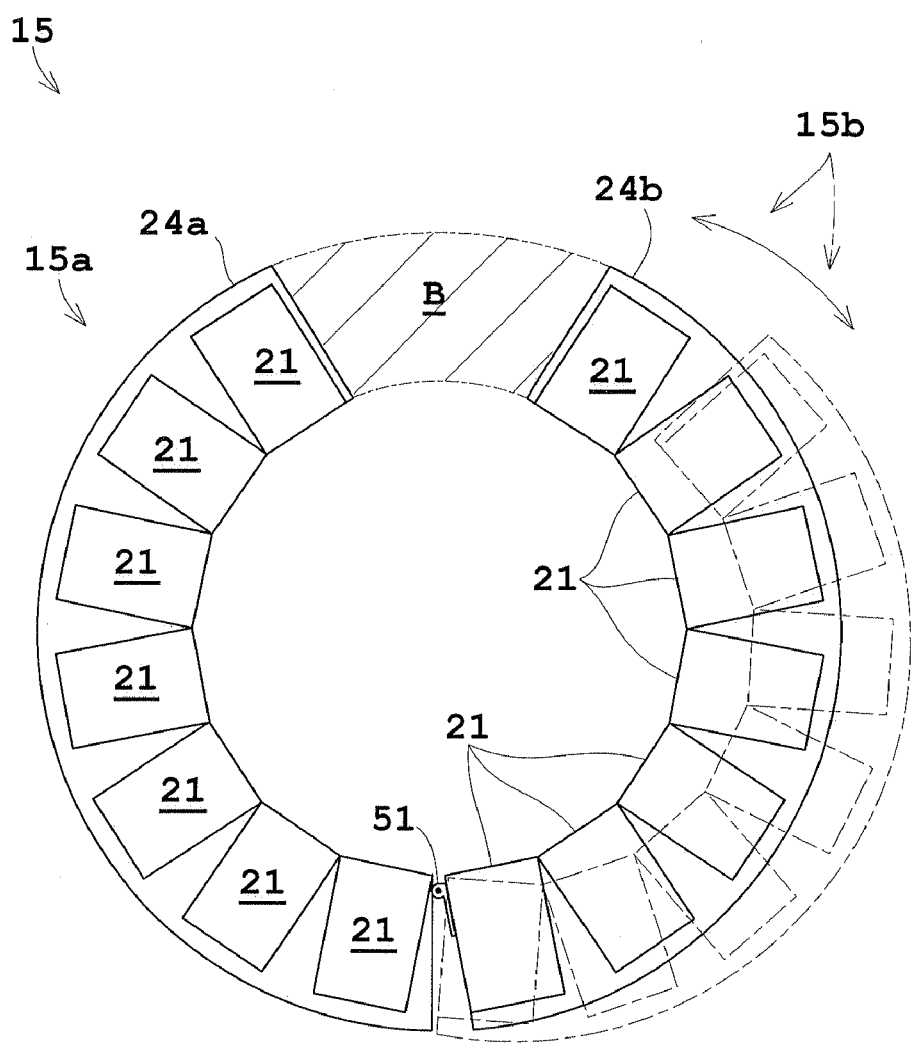
FIG. 9 is a view in horizontal section of a detector according to a modified embodiment.

FIG. 9 refers. FIG. 9 is a view in horizontal section of a detector 15 according to a modified embodiment. The detector 15 is dividable into two split detectors 15*a* and 15*b*. Each of the split detectors 15*a* and 15*b* includes detector blocks 21, and a housing 24*a* or 24*b* for accommodating the detector blocks 21.

The split detectors 15*a* and 15*b* have one ends thereof separated from each other, and a cutout B is formed therebetween. At the other ends, the other ends are joined together so that the detecting planes of the split detectors 15*a* and 15*b* may be continuous. And the split detector 15*b* is pivotably supported by a split pivotal holder 51. The split pivotal holder 51 is disposed in a position adjacent the other ends of the split detectors 15*a* and 15*b*, and holds the split detector 15*b* to be pivotable while maintaining the continuity of the detecting planes of the split detectors 15*a* and 15*b*. This pivoting operation may be stepless, or a stepped pivoting such as in two steps. Because of space for arranging the split pivotal holder 51, even if the detecting planes of the split detectors 15*a* and 15*b* are not strictly continuous, the detecting planes may only be close to one another not to affect diagnosis. Even if the other ends of the split detectors 15*a* and 15*b*, strictly, are not in contact, but a slight gap is formed therebetween, this is included in the joined state as long as the detecting planes are substantially continuous at the other ends.

And with a pivotal movement of the split detector 15*b* caused by a manual operation of the operator, the hollow portion A can be enlarged or reduced in size according to the size, shape and so on of a breast.

In the above modified embodiment, the split detector 15*a* is fixedly installed. However, the split detector 15*a* may also be pivotably held by the split pivotal holder 51.

(7) In the embodiment described hereinbefore, the rotary support 17 supports the detector 11 to be rotatable about one axis P coinciding with the central axis of the hollow portion A. This is not limitative. As one axis P, an axis parallel to the central axis of the hollow portion A can be selected separately. As one axis P, even an axis not parallel to the central axis of the hollow portion A can be selected as appropriate.

(8) In the embodiment described hereinbefore, the breast peripheries to be included in the field of view of the detector 11 are exemplified by the armpit or/and shoulder joint, but these are not limitative. That is, any sites around a breast where breast tissues are present may be selected or varied as appropriate.

(9) The rotary support 17 and the split pivotal holder 51 described hereinbefore are both manually operable. Instead, a drive device may be provided separately.

(10) In the embodiment described hereinbefore, the armrest member 18 is in the form of a curved plate. Without being limited to this, a change may be made to an appropriate shape such as a shape of a flat plate. The armrest member 18 closes the cutout B, but instead can be modified not to close it. That is, the mounting position and shape of the armrest member 18 can be changed as appropriate as long as it can prevent an excessive entry of an arm and a shoulder. As a result, a gap may be formed. The armrest member 18 is for receiving an arm and a shoulder, and is not limited to receiving of only an arm.

(11) In the embodiment described hereinbefore, the detector 11 has the detector blocks 21 stacked in two stages, but this is not limitative. For example, the detector blocks 21 may be in one stage, or three or more stages. The detector 11 is a multilayer ring with scintillator chips 32 arranged in multiple layers. Without being limited to this, a change may be made to have the scintillator chips 32 arranged in one layer only.

Figure 10:
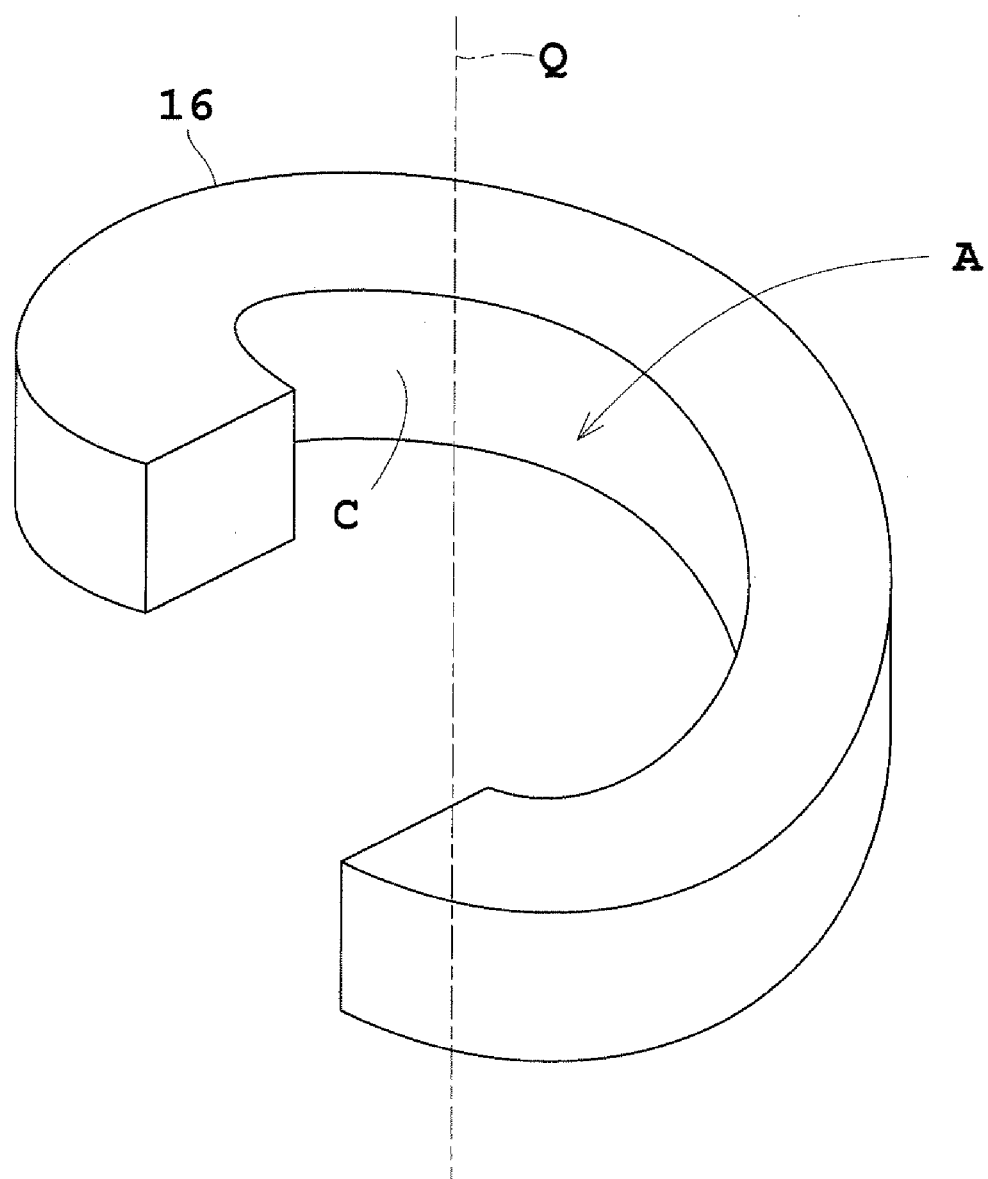
FIG. 10 is a perspective view of a detector according to a modified embodiment.
Figure 11:
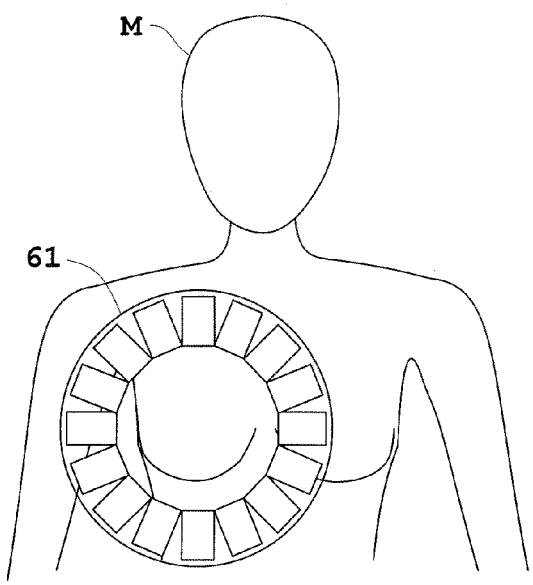
FIG. 11 is a view schematically showing a positional relationship between a detector and a patient according to a conventional example.
Figure 11:
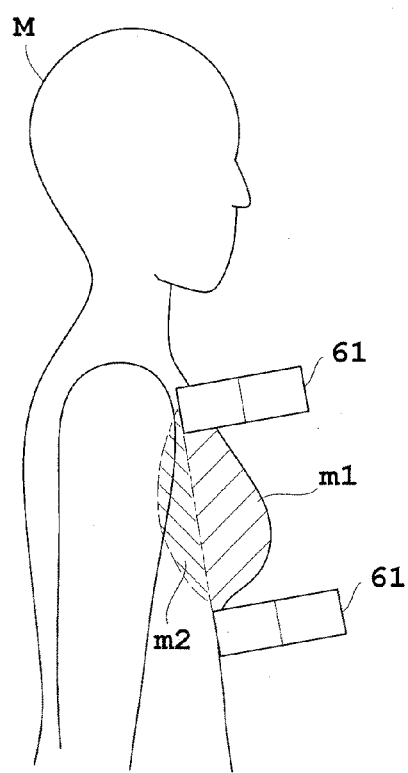

(12) In the embodiment described hereinbefore, the detector 11 is not twisted in the direction of the central axis P of the hollow portion A (that is, the detector 11 from one end to the other end thereof is not displaced relative to the central axis P). This is not limitative. FIG. 10 refers. FIG. 10 is a perspective view of a detector according to a modified embodiment. As shown, a detector 16 may be displaced relative to an axis Q of the hollow portion A. In other words, a change may be made to the detector 16 having a shape twisted in the direction of axis Q of the hollow portion A.

(13) Although the embodiment described hereinbefore provides the detector 11 having the circular hollow portion A, this is not limitative. The shape of the detector may be designed as appropriate based on the body surface or shape of an actual or statistically given patient (human body) M. Specifically, a change may be made to a detector having a shape extending downward from an armpit to a lower part of a breast, turning back along the lower part of the breast, and extending to a shoulder joint above the breast. At this time, it is preferred that the detector is shaped to be placeable along the body surface.

(14) A detector unit for mammography or a nuclear medicine diagnostic apparatus for mammography may be constructed by combining the constructions described in the foregoing embodiment and modifications.

The invention claimed is:

1. A detector unit for mammography comprising a gamma-ray detector having a configuration with a cutout formed in part of a closed curve or a polygon having a hollow portion, the hollow portion providing a field of view.

2. A detector unit for mammography comprising a gamma-ray detector having a configuration with a cutout formed in part of a ring shape having a hollow portion, the hollow portion providing a field of view.

3. The detector unit for mammography according to claim 1, wherein the hollow portion is capable of receiving a breast.

4. The detector unit for mammography according to claim 1, wherein the gamma-ray detector can be positioned so that, when a top of an arm or a shoulder is inserted in the cutout, at least one of an armpit and a shoulder joint, and the breast, enter the field of view of the gamma-ray detector.

5. The detector unit for mammography according to claim 1, wherein the gamma-ray detector has a horseshoe shape or a shape of letter U.

6. The detector unit for mammography according to claim 1, wherein the hollow portion is substantially circular.

7. The detector unit for mammography according to claim 6, wherein the hollow portion is 160 mm to 250 mm in diameter.

8. The detector unit for mammography according to claim 1, wherein the cutout is 50 to 150 mm in length.

9. The detector unit for mammography according to claim 1, wherein the gamma-ray detector has detecting planes vertical to a bottom plane of the hollow portion.

10. The detector unit for mammography according to claim 1, wherein the gamma-ray detector has detecting planes inclined relative to a bottom plane of the hollow portion.

11. The detector unit for mammography according to claim 1, comprising a plate-like object for closing an outside of a field of view at one side of the hollow portion.

12. The detector unit for mammography according to claim 1, comprising an armrest member in form of a flat plate or a curved plate for closing the cutout.

13. The detector unit for mammography according to claim 1, comprising a restricting member disposed in the end regions of the gamma-ray detector for contacting at least one of the top of the arm and the shoulder to restrict entry of the arm and the shoulder to the hollow portion.

14. A detector unit for mammography comprising a gamma-ray detector having a configuration with a cutout formed in a dome shape or conical shape having a cavity, the cavity providing a field of view.

15. The detector unit for mammography according to claim 14, wherein the cavity is capable of receiving a breast.

16. The detector unit for mammography according to claim 14, wherein, when a top of an arm or a shoulder is inserted in the cutout, at least one of an armpit and a shoulder joint, and the breast, can be positioned to enter the field of view of the gamma-ray detector.

17. The detector unit for mammography according to claim 1, comprising a rotary support device for rotatably supporting the gamma-ray detector.

18. The detector unit for mammography according to claim 17, wherein the rotary support device supports the gamma-ray detector to be rotatable about an axis of the hollow portion.

19. A nuclear medicine diagnostic apparatus for mammography comprising:
   a detector unit for mammography according to claim 1; and
   an image processing device for obtaining an RI distribution image based on emission data collected from the detector unit for mammography.

20. The detector unit for mammography according to claim 2, wherein the hollow portion is capable of receiving a breast.

21. The detector unit for mammography according to claim 2, wherein the gamma-ray detector can be positioned so that, when a top of an arm or a shoulder is inserted in the cutout, at least one of an armpit and a shoulder joint, and the breast, enter the field of view of the gamma-ray detector.

22. The detector unit for mammography according to claim 2, wherein the gamma-ray detector has a horseshoe shape or a shape of letter U.

23. The detector unit for mammography according to claim 2, wherein the hollow portion is substantially circular.

24. The detector unit for mammography according to claim 23, wherein the hollow portion is 160 mm to 250 mm in diameter.

25. The detector unit for mammography according to claim 2, wherein the cutout is 50 to 150 mm in length.

26. The detector unit for mammography according to claim 2, wherein the gamma-ray detector has detecting planes vertical to a bottom plane of the hollow portion.

27. The detector unit for mammography according to claim 2, wherein the gamma-ray detector has detecting planes inclined relative to a bottom plane of the hollow portion.

28. The detector unit for mammography according to claim 2, comprising a plate-like object for closing an outside of a field of view at one side of the hollow portion.

29. The detector unit for mammography according to claim 2, comprising an armrest member in form of a flat plate or a curved plate for closing the cutout.

30. The detector unit for mammography according to claim 2, comprising a restricting member disposed in the end regions of the gamma-ray detector for contacting at least one of the top of the arm and the shoulder to restrict entry of the arm and the shoulder to the hollow portion.

31. The detector unit for mammography according to claim 2, comprising a rotary support device for rotatably supporting the gamma-ray detector.

32. The detector unit for mammography according to claim 31, wherein the rotary support device supports the gamma-ray detector to be rotatable about an axis of the hollow portion.

33. A nuclear medicine diagnostic apparatus for mammography comprising:
  a detector unit for mammography according to claim 2; and
  an image processing device for obtaining an RI distribution image based on emission data collected from the detector unit for mammography.

34. The detector unit for mammography according to claim 14, comprising a rotary support device for rotatably supporting the gamma-ray detector.

35. The detector unit for mammography according to claim 34, wherein the rotary support device supports the gamma-ray detector to be rotatable about an axis of the hollow portion.

36. A nuclear medicine diagnostic apparatus for mammography comprising:
  a detector unit for mammography according to 14; and
  an image processing device for obtaining an RI distribution image based on emission data collected from the detector unit for mammography.

* * * * *